United States Patent
Patel (10) Patent No.: US 10,835,688 B2
(45) Date of Patent: Nov. 17, 2020

(54) ENHANCED NEEDLE

(71) Applicant: Tejash Patel, Katy, TX (US)

(72) Inventor: Tejash Patel, Katy, TX (US)

(*) Notice: Subject to any disclaimer, the term of this patent is extended or adjusted under 35 U.S.C. 154(b) by 363 days.

(21) Appl. No.: 15/666,022

(22) Filed: Aug. 1, 2017

(65) Prior Publication Data

US 2019/0038846 A1    Feb. 7, 2019

(51) Int. Cl.
| | |
|---|---|
| *A61M 5/32* | (2006.01) |
| *A61M 5/145* | (2006.01) |
| *A61M 39/28* | (2006.01) |
| *A61M 39/06* | (2006.01) |
| *A61M 25/10* | (2013.01) |
| *A61M 39/02* | (2006.01) |
| *A61B 90/00* | (2016.01) |

(52) U.S. Cl.
CPC ............ *A61M 5/329* (2013.01); *A61M 5/145* (2013.01); *A61M 25/10183* (2013.11); *A61M 39/0247* (2013.01); *A61M 39/06* (2013.01); *A61M 39/28* (2013.01); *A61B 2090/064* (2016.02); *A61M 2039/027* (2013.01); *A61M 2039/0258* (2013.01); *A61M 2039/0261* (2013.01); *A61M 2039/0273* (2013.01); *A61M 2205/332* (2013.01); *A61M 2205/502* (2013.01)

(58) Field of Classification Search
CPC .......... A61M 1/0084; A61M 25/10183; A61M 5/145; A61M 5/329
USPC ...................................................... 604/98.02
See application file for complete search history.

(56) References Cited

U.S. PATENT DOCUMENTS

| | | | | |
|---|---|---|---|---|
| 3,952,742 | A | * | 4/1976 | Taylor ............... A61M 25/0606 604/21 |
| 4,217,895 | A | * | 8/1980 | Sagae ................. A61M 5/1582 604/167.01 |
| 4,634,427 | A | | 1/1987 | Hannula et al. |
| 4,861,341 | A | * | 8/1989 | Woodburn ............ A61M 5/158 604/175 |
| 5,653,230 | A | | 8/1997 | Ciaglia et al. |
| 5,662,674 | A | * | 9/1997 | Debbas .............. A61B 17/3403 604/96.01 |
| 5,807,329 | A | * | 9/1998 | Gelman ............ A61M 25/0026 604/102.02 |

(Continued)

OTHER PUBLICATIONS

International Search Report. WO02019027582. Published Sep. 4, 2018 (Year: 2018).*
PCT Search Report (PCT/US2018/038562), dated Sep. 4, 2018.

*Primary Examiner* — Brandy S Lee
*Assistant Examiner* — Nidah M Hussain
(74) *Attorney, Agent, or Firm* — Gregory L. Porter; Hunton Andrews Kurth LLP (57) ABSTRACT

A port-a-cath needle adapted for determining the position of the needle prior to dispensing medical treatments is disclosed. Disclosed embodiments of the port-a-cath needle comprises a cannula, a hollow needle, and an inflatable balloon. The balloon is disposed at the distal end of the port-a-cath needle such that when the needle is inserted into a patient, the balloon may be inflated and the resistance pressure used to determine if the needle is inserted into the port chamber or a port-a-cath device or is surrounded by soft tissue. In certain embodiments, the balloon may be maintained in the inflated configuration in order to help retain the port-a-cath needle within the port chamber while treatment is delivered to the patient.

16 Claims, 5 Drawing Sheets

(56) References Cited

U.S. PATENT DOCUMENTS

| | | |
|---|---|---|
| 6,685,648 B2 | 2/2004 | Flaherty et al. |
| 8,090,430 B2 | 1/2012 | Makower et al. |
| 9,669,197 B2 * | 6/2017 | Robertson ............. A61M 29/02 |
| 2007/0179440 A1 | 8/2007 | Putz |
| 2008/0114338 A1 | 5/2008 | Kumar |
| 2010/0049184 A1 | 2/2010 | George et al. |
| 2012/0101515 A1 | 4/2012 | Barbod |
| 2012/0209166 A1 * | 8/2012 | Power .................... A61M 11/00 604/24 |
| 2013/0023770 A1 * | 1/2013 | Courtney ................ A61B 8/12 600/467 |
| 2014/0135809 A1 * | 5/2014 | Robertson .......... A61B 17/3421 606/191 |
| 2016/0089181 A1 * | 3/2016 | Johnson ............. A61B 17/0218 600/424 |

\* cited by examiner

ENHANCED NEEDLE

FIELD

Embodiments described herein relate to needles, ports, port-a-cath needles, and other medical devices which may be useful for delivering medications and/or treatments to a patient. More particularly, some embodiments relate to an enhanced needle and method for confirming the position of a needle within a port.

BACKGROUND AND SUMMARY

Port-a-cath needles are used to access port-a-cath devices. Port-a-cath devices are typically permanently implanted under the skin of patient and facilitate delivery of chemotherapy drugs, IV fluids, medications, TPN, or other treatments. Port-a-cath devices typically include an internal chamber, sealed with a self-sealing septum, and a catheter tube which connects the chamber to the vein of a patient. This allows for repeated and/or periodic injections or infusions to be performed by piercing the self-healing septum of the port chamber using an injection device, such as a port-a-cath needle, and delivering the treatment into the port chamber. The treatment then flows from the chamber through the catheter tube into the veins of the patient. This arrangement allows for the delivery of treatments which may be irritating or damaging to the skin or soft tissue as is commonly necessary when treating hematology and/or oncology patients. Potential treatments include, but are not limited to, vesicants, irritants, infusions, and other medications. Port-a-cath devices may also be known as or include implantable venous access devices and are known in the art.

Current port-a-cath needles are placed into the port chamber and may be secured in place using tape or dressing. Port-a-cath needles are typically intended to extend down to the bottom of the port chamber to help confirm their placement into the correct location. A common problem associated with this arrangement is that the port-a-cath needles sometimes do not extend to the bottom of the port chamber or may only be partially placed in the port chamber or they may be placed in the surrounding soft tissue rather than within the port chamber. This can lead to the release of medical treatments into soft tissue rather than the port chamber. This can cause tissue damage and even possible tissue necrosis requiring surgery in the case of certain vesicant chemotherapies. The leakage of chemotherapy or other treatments into the soft tissue under the skin has been known to cause the loss of breast tissue in some cases. There are also situations in which the port-a-cath needle may become dislodged from the port chamber due to pulling on the needle. In these cases, the chemotherapy may leak onto the soft tissue as well as the external skin creating a safety hazard as well as possible tissue irritation/damage.

What is needed is a device, method, and/or system allowing medical staff to confirm the proper placement of the tip of a needle which can be performed rapidly and with only modest amounts of training.

Embodiments disclosed include a port-a-cath needle with an inflatable balloon at the distal portion. This allows medical staff to inflate the balloon and use the resistance pressure to inflation to judge if the port-a-cath needle is inserted into the port chamber or soft tissue. The inflatable balloon may additionally and/or alternatively help to secure the port-a-cath needle in the proper position and reduce the chance of the needle getting inadvertently pulled out of the port chamber. The methods, devices, and system disclosed could serve to reduce errors in treatment delivery and allow for improved medical safety.

DETAILED DESCRIPTION

Figure 1:
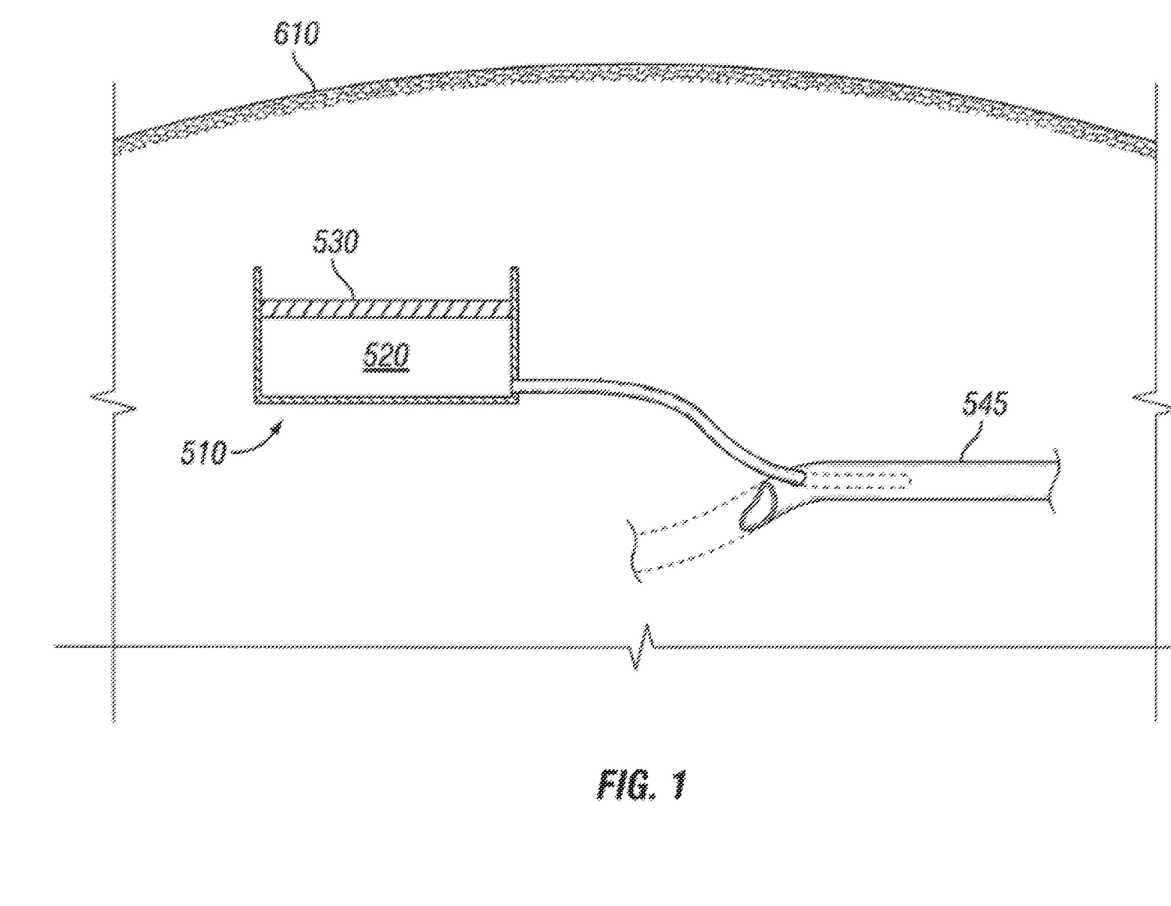
FIG. 1 depicts a port-a-cath device including an internal chamber and catheter tube providing access to a vein.
Figure 2A:
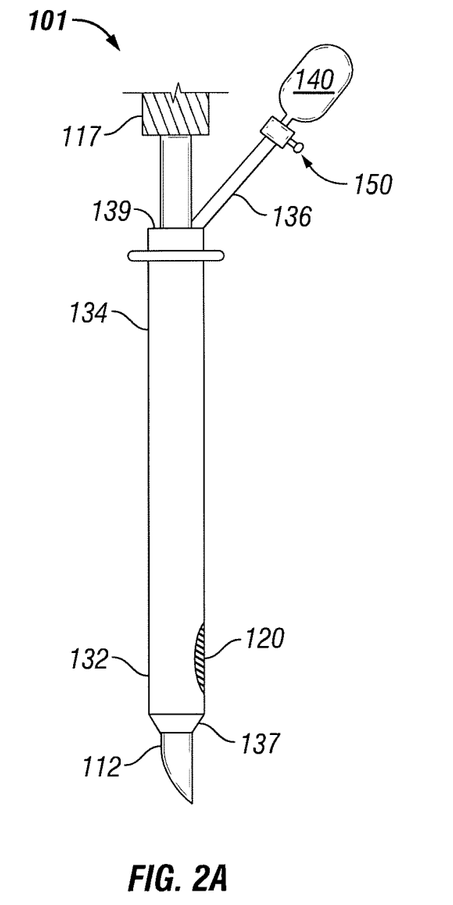
FIG. 2A depicts one embodiment of a port-a-cath needle with a balloon in the deflated configuration.
Figure 2B:
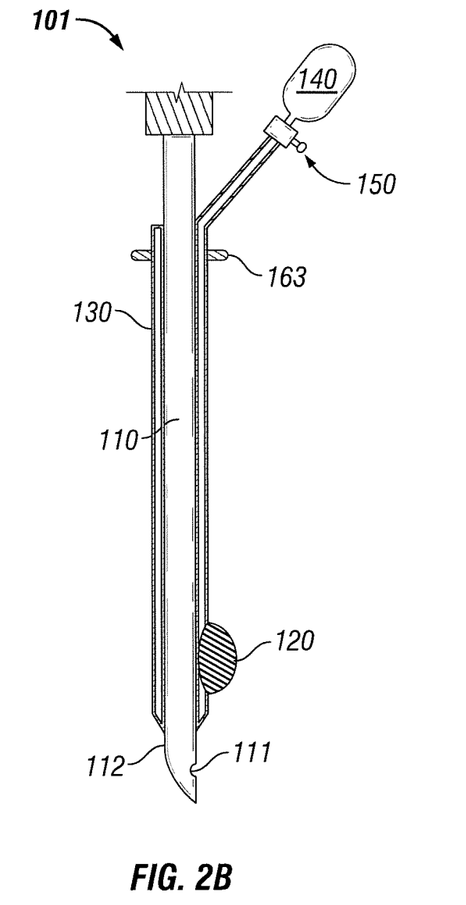
FIG. 2B shows a cut-away view of one embodiment of a port-a-cath needle with a balloon in the inflated configuration.

Disclosed embodiments of the port-a-cath needle 101 for the delivery of medical treatment into a port-a-cath device comprises a cannula 130, a hollow needle 110, and an inflatable balloon 120. In many embodiments, the cannula 130 forms an exterior portion of the port-a-cath needle 101 and the balloon 120 is incorporated into the cannula 130. In these embodiments, the hollow needle 110 is encased within the cannula 130 as shown in FIGS. 2A and 2B. The hollow needle 110 has a proximal end 114, which may connect to a standard hub 117 to connect the hollow needle 110 to a syringe. The hollow needle 110 also has a distal end 112 which may be used for delivering treatment 330 to a patient. The cannula has a distal balloon end 132 and a proximal pressure end 134. In some embodiments, the cannula proximal portion 134 may be a spout 136 in fluid communication with the main body of the cannula 130. In the embodiments depicted in FIGS. 2A and 2B, the space between the hollow needle 110 and the cannula 130 is in fluid communication with the balloon 120 and a bulb 140 or other device for supplying pressure to the balloon 120. In these embodiments, the hollow needle 110 may be sealed within the cannula 130 such that the cannula 130 may receive pressure from the bulb 140 and communicate that pressure to the balloon 120 without leaking any pressurized fluid. The materials and methods for sealing the hollow needle 110 to the cannula 130 are well known and understood in the art. The hollow needle 110 and the cannula 130 are in a fixed positional relationship relative to each other and do not substantially slide or rotate relative to each other.

In some embodiments, the proximate portion of the hollow needle 114 is sealed to the proximate portion of the cannula 134 forming a proximate junction 139 and the distal portion of the hollow needle 112 is sealed to the distal portion of the cannula 132 forming a distal junction 137. This arrangement isolates the interior of the hollow needle from the interior of the cannula. In some embodiments, the distal junction 137 connecting the distal portion of the cannula 132 to the distal portion of the hollow needle 112 may be tapered, angled, or chamfered to reduce or minimize catching, pulling, or otherwise causing strain on the skin or tissue of the patient or the septum of the port-a-cath device when the port-a-cath needle 101 is inserted into a patient and through the septum 530 of a port-a-cath device.

FIG. 2A shows the exterior of an embodiment of a port-a-cath needle 101 in which the cannula 130 forms the majority of the exterior of the port-a-cath needle 101. The cannula 130 seals around the majority of the hollow needle 110. The distal portion of the hollow needle 110 exits the cannula 130 so that treatment 330 may be delivered through opening 111. The proximal portion of the cannula 130 seals around the proximate portion of the hollow needle 110 such that pressure delivered to the proximal portion of the cannula 134 is transferred to the balloon 120. In some embodiments, the proximal portion of the cannula 134 may comprise a separate spout 136 in fluid communication with the cannula 130. The spout 136 may facilitate the connection of pressure bulb 140, clamp 150, and other components of the port-a-cath needle 101. In many embodiments, spout 136 will be integrated into a single piece cannula 130.

FIG. 2B shows a cut-away view of the embodiment disclosed in FIG. 2A. This figure clarifies the positional relationship between the hollow needle 110 and the cannula 130 and shows that a narrow gap exists between the exterior wall of the hollow needle 110 and the interior wall of the cannula 130. This gap allows pressure applied to the proximal portion of the cannula 134 to be transferred to the balloon 120.

In other embodiments, the hollow needle 110 may form an exterior portion of the port-a-cath needle 101. In these embodiments, the inflatable balloon 120 is incorporated into the hollow needle 110 at the distal end 112. In these embodiments, cannula 130 is in fluid communication with the inflatable balloon 120 which allows the balloon 120 to be inflated using a bulb 140 or other device for delivering a liquid or gas under pressure to the balloon 120. In these embodiments, cannula 130 is disposed within the hollow needle 110 as shown in FIGS. 3A-3D. FIGS. 3A-3D also disclose multiple optional features of the port-a-cath needle 101 which may be incorporated into many other embodiments of the port-a-cath needle 101.

Many embodiments will also comprise a valve, clamp 150, and/or screw device for optionally disrupting fluid communication between the inflatable balloon 120 and the exterior environment, thereby maintaining pressure within the balloon 120 and locking the balloon 120 in the inflated position.

When the balloon 120 is in the deflated configuration, it lies substantially flush with the exterior surface of the port-a-cath needle 101. This prevents the deflated balloon 120 from interfering with inserting the needle through the skin and soft tissue of the patient as well as through the septum 530 of the port-a-cath chamber 520. In some embodiments, the balloon 120 may be slightly recessed relative to the exterior surface of the port-a-cath needle 101 while it is deflated. The balloon 120 may be made of any material suitable for inserting into a patient. Many of the disclosed embodiments are intended for single use only, thus the durability of the balloon material to withstand several independent rounds of being inflated and deflated is not a significant concern.

The cannula 130 in fluid communication with the inflatable balloon 120 allows the balloon 120 to be inflated and deflated. The cannula 130 may be made of polymer, metal, silicon, rubber, or any other suitable material or combination of materials. Many embodiments will utilize a manual squeeze bulb 140 to deliver air under pressure to the balloon 120, thereby inflating the balloon. The squeeze bulb 140 may be connected to the cannula 130 using any of the connection methods and devices known in the art. As is known in the art, squeezing the bulb 140 will create pressure within the bulb 140. That pressure will then be communicated through the cannula 130 to the balloon 120 causing the balloon 120 to inflate. This arrangement allows for the immediate detection of any resistance to inflation of the balloon 120 by the medical staff. The level and nature of this resistance may inform the medical staff inflating the balloon 120 as to the positioning of the port-a-cath needle 101. As an example only, if the port-a-cath needle 101 is inserted into the internal chamber 520 of a port-a-cath device 510, the balloon 120 will be in a relatively empty or fluid-filled space with minimal solid objects exerting pressure on the balloon 120 and resisting its inflation. If the port-a-cath needle 101 is not inserted into the internal chamber 520 of a port-a-cath device 510 and the distal portion of the port-a-cath needle 101 is surrounded by soft tissue 610, this soft tissue 610 will exert an external pressure on the balloon 120, thereby resisting its inflation. Similarly, if the port-a-cath needle 101 is inserted only slightly into the port chamber 520 such that the balloon 120 is surrounded by the self-sealing septum 530, the resistance to inflation will be significantly increased as compared to inflating the balloon 120 within the port chamber 520. The increase in resistance pressure can be detected by the medical staff as they attempt to inflate the balloon 120 using the manual squeeze bulb 140. The detected increase in pressure informs the medical staff that the port-a-cath needle 101 may be improperly positioned prior to delivering treatment 330. This can avoid the delivery of treatment 330 directly into the soft tissue 610 as opposed to the port-a-cath device 510 or veins 545 of the patient. Delivering treatment 330 when the port-a-cath needle 101 is not properly positioned in the port-a-cath chamber 520 can result not only in wasted medical materials, but some treatments 330 can irritate or damage the surrounding tissues requiring additional medical attention and possibly surgery.

Alternate embodiments may use alternative sources of pressurized air or other gases or liquids, such as saline 620 or other medically appropriate liquids, to inflate the balloon 120 instead of the manual squeeze bulb 140. In these embodiments, a pressure regulator 250 may be required in order to ensure that the balloon 120 is not maximally inflated when the port-a-cath needle 101 is inserted into soft tissue 610. A pressure regulator 250 may also prevent the balloon 120 from being over inflated, rupturing, or inflating too rapidly. If the balloon 120 is significantly inflated while the port-a-cath needle 101 is inserted into soft tissue 610 rather than the port chamber 520, this could cause the patient to experience pain and, in some cases, the surrounding tissue could be damaged by the physical pressure exerted by the balloon 120. A pressure regulator 250 could be used in order to ensure that only mild pressure is ever applied to inflate the balloon 120, thereby reducing or eliminating the chance of damaging any surrounding tissues. The pressure regulator 250 may be incorporated directly into the port-a-cath needle device or may be attached to a pressurized line upstream of the port-a-cath needle 101.

Disclosed embodiments may rely on a pressure sensor 210 to monitor the amount of pressure resisting inflation of the balloon 120. The pressure sensor 210 may be disposed anywhere in fluid communication with the cannula 130 and balloon 120. In these embodiments, a pressure sensor 210 and/or pressure sensor display 215 may be used to objectively inform the medical staff of the amount of resistance pressure as opposed to relying on the subjective determination of the medical staff. The pressure sensor display 215 may be digital or analog. A pressure sensor 210, in combination with a pressure regulator 250, may also be used to automatically adjust the amount of pressure applied to inflate the balloon 120.

In certain embodiments, a pressure sensor 210, in combination with a clamp 150, valve, or similar device could be used as a fail-safe in order to ensure that the amount of pressure used to inflate the balloon 120 never exceeds a pre-determined amount. In such embodiments, the pre-determined amount could be set at a pressure lower than the amount required to cause damage to any surrounding tissues in the event that the balloon 120 was surrounded by soft tissue 610 when pressure was applied to inflate the balloon 120.

Figure 5:
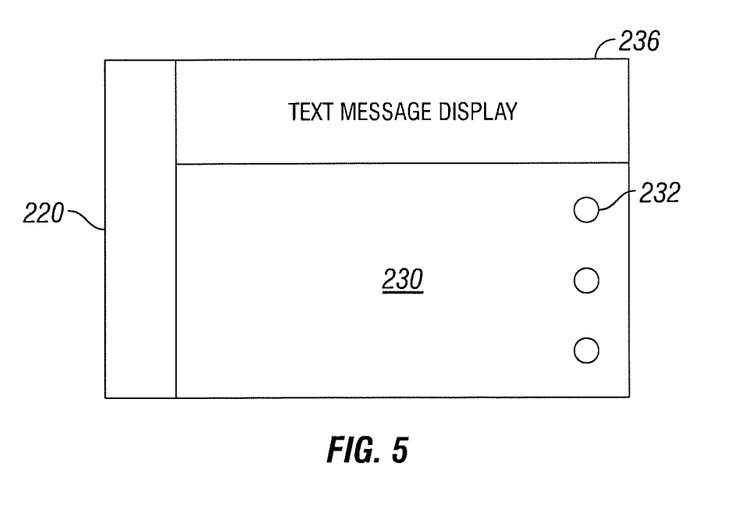
FIG. 5 depicts one embodiment of an alarm unit including a processor, indicator lights, and text message display.
Figure 6:
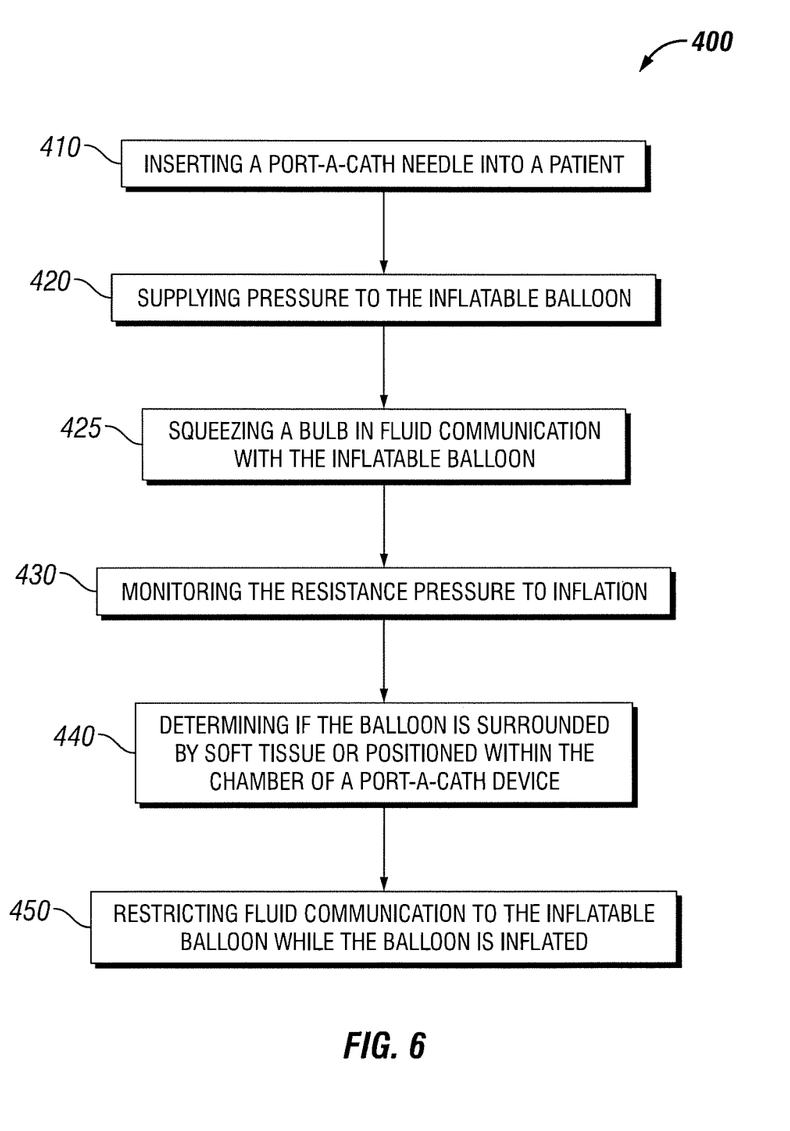
FIG. 6 depicts a potential method of determining the location of a port-a-cath needle.

In some embodiments, a processor 220 may be operably connected to a pressure sensor 210 and be arranged to gather and analyze data from the pressure sensor 210. The processor 220 may be connected to an alarm 230 or other form of notification system. The processor 220 may activate the alarm 230 in response to a predetermined condition. For example purposes only, if the processor 220 determines that the data from the pressure sensor 210 is indicative of the balloon 120 being inflated while surrounded by tissue, the processor 220 may activate an alarm 230 alerting the medical staff to the conditions. The alarm 230 may take the form of indicator lights 232, an audible alert, a text message display 236, or any other manner of informing the staff. In some embodiments, the processor 220 may be able to determine if the balloon 120 is positioned in the self-sealing septum 530 and may inform the staff to insert the port-a-cath needle 101 deeper into the port chamber 520. The processor 220 may also be connected to a pressure regulator 250 which may be automatically closed if the processor 220 detects a dangerous condition such as excessively high pressure readings. In some embodiments, the processor 220 may control the pressure regulator 250 in order to automate the inflation of the balloon 120. In these embodiments, the processor 220 may allow pressure to begin inflating the balloon 120 while monitoring the resulting pressure data. If the pressure data corresponds with the balloon 120 inflating within the port chamber, the processor can alert the staff that the port-a-cath needle 101 is properly positioned. If the processor 220 determines that the pressure data corresponds to the balloon 120 being inserted into the septum 530 or the soft tissue 610, it can alert the medical staff to these conditions and instruct them accordingly. The processor 220 may similarly be connected to a pressure release valve 170 and be arranged to release the pressure in the balloon 120 if the pressure exceeds a certain threshold. This pre-determined threshold can be set to an amount of pressure less than the amount required to damage soft tissue 610.

In some embodiments, a pre-determined amount of pressurized air, or other gas or liquids, could be used to inflate the balloon 120 and the resulting pressure could be used in order to determine the proper placement of the needle 110. For example purposes only, if 1 cc of pressurized saline were used to inflate the balloon 120, the resulting resistance pressure would be expected to be lower if the balloon 120 were inflated within the port-a-cath chamber 520 as opposed to being inflated while surrounded by soft tissue 610 or the port septum 530.

Figure 3A:
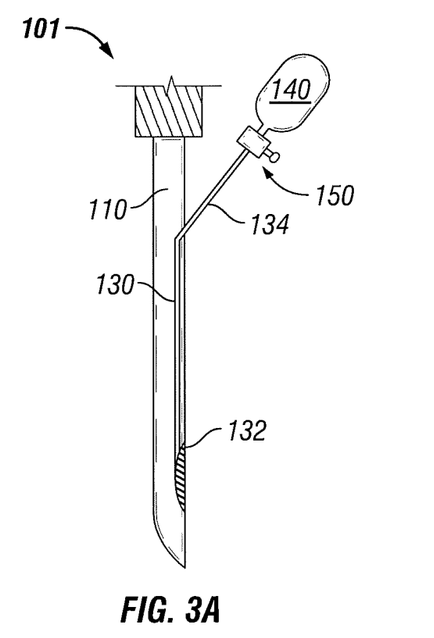
FIG. 3A depicts an embodiment of a port-a-cath needle with a deflated balloon.
Figure 3B:
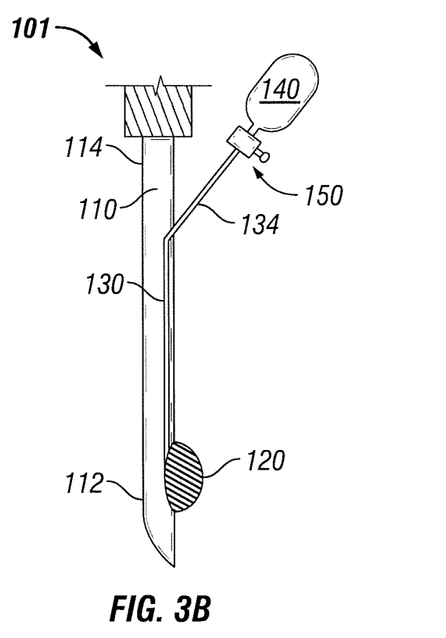
FIG. 3B depicts an embodiment of a port-a-cath needle with an inflated balloon.
Figure 3C:
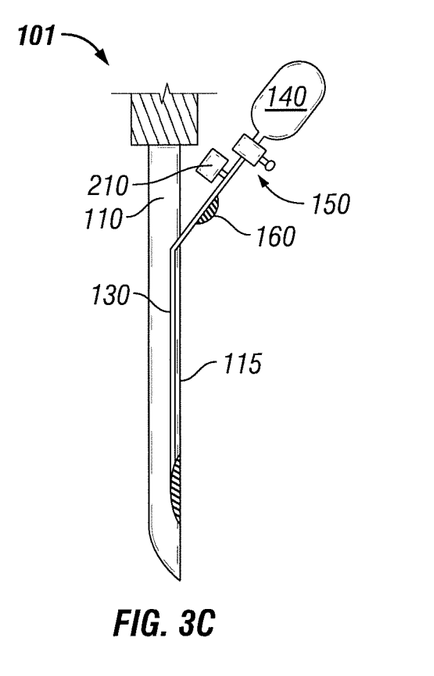
FIG. 3C depicts one embodiment of a port-a-cath needle utilizing a rupture membrane.

In alternative embodiments, a rupture membrane 160 may be incorporated into the port-a-cath needle 101. This represents a safe and comparatively low-cost option for preventing excessive pressure from being used to inflate the balloon 120. In this embodiment, a rupture membrane 160 could be incorporated into the cannula 130 such that if the amount of pressure in the cannula 130 were to exceed a certain pressure threshold, the rupture membrane 160 would burst, releasing the pressurized air or other gas or liquid, within the cannula 130 and balloon 120 to the outside environment. In certain embodiments, it may be advantageous to position a rupture membrane 160 at the proximate portion of the cannula 134 such that the rupturing of the membrane would minimally impact the hollow needle 110 or the treatment.

Some embodiments of the port-a-cath needle 101 may comprise an external hilt 163 for ensuring that the port-a-cath needle 101 may only be inserted a certain depth into the patient.

In addition to inflating the balloon 120 with air, other gasses or liquids may be used alternatively or as well. In some embodiments, a self-contained reservoir of saline solution or other medically appropriate liquid may be used to inflate the balloon. In alternative embodiments, inflating the balloon with a particular liquid may facilitate identifying the position of the needle using scanning technologies such as ultrasound, fluoroscopy, X-ray, CT, or MRI.

In addition to using the resistance pressure when inflating the balloon 120 as an indicator of the position of the port-a-cath needle 101, in some embodiments, a valve, clamp 150, or other locking device may be used to maintain the balloon 120 in its inflated configuration. If the balloon 120 is inflated while it is inside the port chamber 520, the inflated balloon 120 may prevent accidental withdrawal of the port-a-cath needle 101 through the self-sealing septum 530. This may be particularly useful when delivering infusions which require the port-a-cath needle 101 to remain in place for an extended period of time. These two benefits of the balloon 120 may be utilized in several methods. FIG. 5 outlines one such method. In method 400, the medical staff inserts the port-a-cath needle into a patient 410. Then the medical staff may attempt to inflate the balloon 420 and monitor the resistance pressure to inflation 430. The medical staff may use the resulting resistance pressure in order to determine whether the port-a-cath needle has been properly inserted into the port chamber or is surrounded by soft tissue 440. Once the port-a-cath needle has been properly inserted into the port chamber, the balloon may be inflated and the medical staff may tighten a valve or engage a clamp 450 in order to maintain the balloon in the inflated configuration. This will prevent the port-a-cath needle from being accidentally withdrawn through the port chamber septum. In some embodiments, the port-a-cath needle 101 may be bent at least 30°, or at least 45°, or at least 60°, or at least 90° so that the port-a-cath needle 101 may be taped or otherwise secured in position for the duration of an infusion.

The port-a-cath needle 101 may be made from conventional materials such as stainless steel as is known in the art. In some embodiments, the port-a-cath needle 101 may be made using materials suitable for medical implants such as titanium, and/or zirconium. In some cases, the port-a-cath needle 101 may remain in position for an extended period of time, such as when delivering an infusion. In these cases, potential allergic reactions may be avoided by using materials that are less than 10% or less than 5% or less than 1% or less than 0.1% nickel, cobalt, chromium, aluminum, vanadium, niobium and/or combinations or alloys thereof.

Figure 3D:
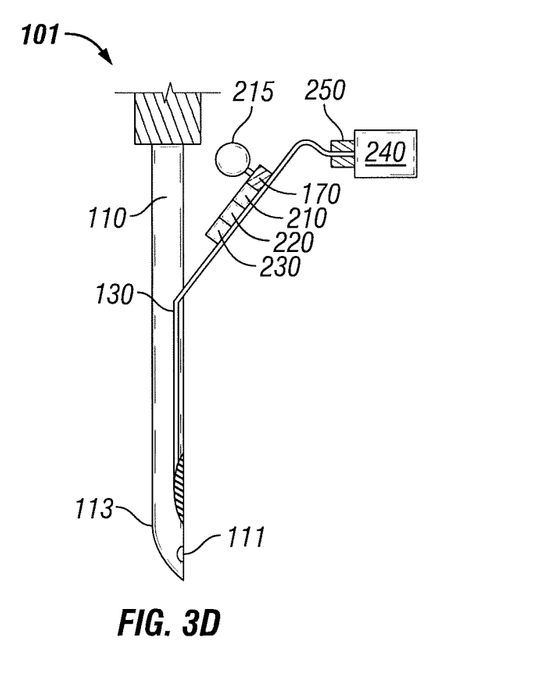
FIG. 3D depicts one embodiment of a port-a-cath needle showing the positioning of the needle opening.

The hollow needle 110 may utilize any type of tip 113. The hollow needle 110 may include a Huber point tip, beveled tip including but not limited to 20° bevel tip, domed tip, domed side hole tip, eccentric tip or any other needle tip. Preferred embodiments will use a non-coring tip 113 with an opening 111 for dispersing treatments 330 disposed on the side of the hollow needle 110. In most embodiments, the balloon 120 will be disposed slightly proximally to the opening 111 in order to ensure that the opening 111 is at least as deeply inserted into the port chamber 520 as the inflatable balloon 120. In alternative embodiments, the balloon 120 may be disposed distally of the opening 111.

The bore length of the hollow needle 110 may be as short as ⅜", or as short as ½", or as short as ⅝", or as short as ¾", or as short as 1". In some embodiments, the bore length may also be as long as 1", or as long as 1¼", or as long as 1½", or as long as 2", or as long as 3" or even longer.

Figure 4A:
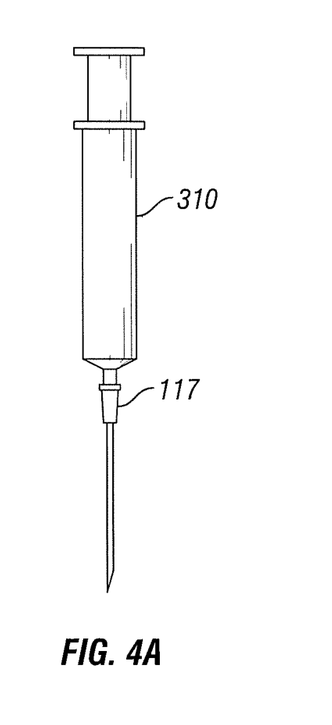
FIG. 4A depicts a simplified version of a port-a-cath needle connected to a syringe.
Figure 4B:
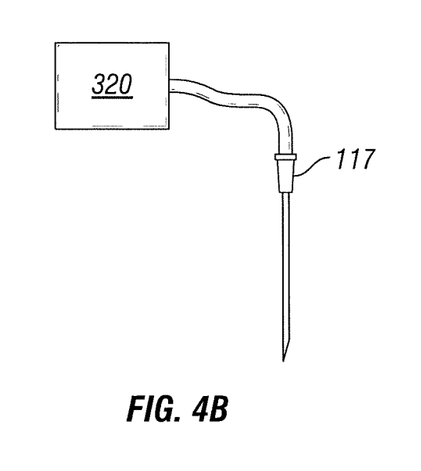
FIG. 4B depicts a simplified version of a port-a-cath needle connected to an infusion pump.

The port-a-cath needle 101 may incorporate a standard twist-mount hub 117 for connecting a standard twist-mount syringe 310 or may incorporate a slip or push-on connection, luer lock connection, or any other appropriate connection known in the art. In these embodiments, a conventional syringe 310 may be used to deliver the treatment 330 through the hollow needle 110 into the port-a-cath chamber 520. In some embodiments, the syringe 310 may be replaced with an infusion pump 320 or other device for delivering the treatment 330. In these embodiments, the port-a-cath needle hub 117 must be appropriate to connect to the desired treatment delivery device. FIGS. 4A and 4B depict highly simplified versions of the port-a-cath needle connected to a syringe and infusion pump respectively.

Alternative embodiments will comprise an automatic port-a-cath needle injection device which may or may not include an inflatable balloon as described above. The training and certification process frequently required for medical staff to utilize port-a-cath devices is not typically required for all medical staff. In some situations, a patient may have a port-a-cath device implanted but the available medical staff is not trained, certified, and/or approved to access the port-a-cath device to deliver treatment. In some instances, this can result in a patient receiving multiple painful injections or attempted injections when a single injection to access the port-a-cath device would provide a beneficial alternative.

An automatic port-a-cath injection device comprises a sensor for detecting the implanted port-a-cath device. Detection of the port-a-cath device is traditionally performed manually by medical staff. Standard port-a-cath devices contain a number of physical protrusions which can be physically detected by pressing on the skin of the patient until the protrusions are felt by the medical staff. The location of the port-a-cath chamber can then be extrapolated based on the locations of the protrusions.

The disclosed automatic port-a-cath injection device comprises sensors for automatically detecting the location of the implanted port-a-cath device. The automatic injection device can detect the location of the implanted port-a-cath device and inform the medical staff of the proper location and angle of the automatic injection device in order to accurately and reliably insert a port-a-cath needle into the port-a-cath device implanted within a patient.

In order to automatically detect the proper location of the port-a-cath device, the automatic port-a-cath injection device uses at least one, and possibly more than one, type of sensor capable of locating a port-a-cath device. Possible port-a-cath device sensors include magnetic sensors, light and photon-based sensors, ultrasound devices, electromagnetic field based sensors, and near field communication devices. Many of these sensors necessarily contain integral transmission/emission devices which are well known in the art. These sensors can be arranged to detect a standard port-a-cath device, which typically contains polymer and/or metal materials which may be readily distinguished from the patient's tissues by an arrangement of transmission/detection devices.

In some embodiments, a modified port-a-cath device may be used which contains an RFID chip, signal transmission device, or near field communication device integrated into the implanted port-a-cath device. Use of a modified port-a-cath device may facilitate the port-a-cath device being located by a sensor in the automatic port-a-cath injection device.

The port-a-cath device sensors are operably connected to a processor which is configured to analyze the sensor data and provide an output to the medical staff regarding the location of the port-a-cath device relative to the automatic port-a-cath injection device. This output can include at least location data regarding the relative location of the port-a-cath device as well as angular alignment data in order to ensure that the port-a-cath needle is accurately inserted into the internal port-a-cath chamber. The incorporation of angular alignment data helps to avoid the potential system of the automatic port-a-cath injection device being properly located over the implanted port-a-cath device but the port-a-cath needle being inserted into the patient at an angle which causes the port-a-cath needle to miss the septum of the internal port-a-cath chamber.

Once the automatic two devices are properly aligned, the automatic injection device indicates the proper alignment to the medical staff who inserts a port-a-cath needle into the patient, accessing the port-a-cath device in order to deliver treatment to the port-a-cath chamber. In some embodiments, the automatic port-a-cath injection device contains a motor, actuator, piston, or similar device for inserting a port-a-cath needle into the patient automatically once the device is properly aligned. In some of these embodiments, the automatic port-a-cath injection device is connected to a supply of pressurized air or other fluid. In these embodiments, the pressurized air may be used to provide the force necessary for inserting the port-a-cath needle into the patient. Certain embodiments insert a port-a-cath needle which comprises an inflatable balloon as described above. In these embodiments, the same pressurized fluid which drives the injection of the port-a-cath needle may be used to inflate the balloon in order to confirm proper placement of the port-a-cath needle.

The automatic port-a-cath injection device is configured to receive disposable needles, including disposable port-a-cath needles with an inflatable balloon. These needles fit into a carriage which allows the automatic port-a-cath injection device to insert the port-a-cath needles into the patient without contaminating the injection device itself. In many embodiments, the injection device comprises a housing which has retaining clips for single-use medical tubing used for delivering treatment to the patient through the port-a-cath needle.

Certain embodiments of the automatic port-a-cath injection device comprise a pressure regulator, a pressure sensor, a port-a-cath device sensor, a carriage for inserting a port-a-cath needle prior to insertion into the patient, an actuator for inserting the port-a-cath needle into the patient, and a tube in fluid communication with the port-a-cath needle which allows treatment to be delivered through the automatically injected port-a-cath needle.

Disclosed embodiments relate to a port-a-cath needle comprising a cannula wherein the cannula has a distal portion and a proximate portion; a hollow needle wherein the hollow needle has a distal portion and a proximate portion; and an inflatable balloon, wherein the balloon is in fluid communication with the cannula. In certain embodiments, the hollow needle is at least partially sealed within the interior of the cannula, wherein the proximate portion of the hollow needle is sealed to the proximate portion of the cannula forming a proximate junction and the distal portion of the hollow needle is sealed to the distal portion of the cannula forming a distal junction, and wherein the interior of the hollow needle is isolated from the interior of the cannula, and wherein the inflatable balloon is positioned at the distal portion of the cannula. In some embodiments, the distal junction is tapered. In certain embodiments, the cannula has an exterior surface and the inflatable balloon is arranged to be substantially flush with the exterior surface of the cannula when the balloon is not inflated. Disclosed embodiments may also relate to a port-a-cath needle wherein the inflatable balloon is positioned at the distal portion of the hollow needle.

Some embodiments, may further comprise a squeeze bulb in fluid communication with the proximate portion of the cannula; a clamp wherein the clamp is arranged to optionally restrict fluid communication with the cannula; a processor; a pressure sensor, wherein the processor is operably connected to the pressure sensor and configured to analyze data from the pressure sensor; a source of pressurized fluid in fluid communication with the proximate portion of the cannula; a pressure regulator, wherein the processor is operably connected to the pressure regulator; a clamp wherein the clamp is arranged to optionally restrict fluid communication of the cannula, wherein the processor is operably connected to the clamp; a rupture membrane in fluid communication with the cannula, wherein the membrane is arranged to rupture in response to pressure exceeding a pre-determined threshold; a syringe in fluid communication with the hollow needle; and/or an infusion pump in fluid communication with the hollow needle. In certain embodiments, the hollow needle has a non-coring tip.

Disclosed embodiments may relate to a port-a-cath system comprising a vascular access port comprising an internal chamber, wherein the internal chamber is sealed using a self-sealing septum and wherein the internal chamber is in fluid communication with a catheter; and a port-a-cath needle, wherein the port-a-cath needle comprises a cannula wherein the cannula has a distal portion and a proximate portion; a hollow needle wherein the hollow needle has a distal portion and a proximate portion; and an inflatable balloon, wherein the balloon is in fluid communication with the cannula. Some embodiments may further comprise a squeeze bulb in fluid communication with the cannula.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A port-a-cath needle comprising:
    a cannula wherein the cannula has a distal portion and a proximate portion;
    a hollow needle wherein the hollow needle has a distal portion and a proximate portion; and
    an inflatable balloon, wherein the inflatable balloon is in fluid communication with the cannula;
    wherein the hollow needle is at least partially sealed within an interior of the cannula, wherein the proximate portion of the hollow needle is sealed to the proximate portion of the cannula forming a proximate junction and the distal portion of the hollow needle is sealed to the distal portion of the cannula forming a distal junction, wherein an interior of the hollow needle is isolated from the interior of the cannula, and wherein the inflatable balloon is positioned at the distal portion of the cannula and wherein the hollow needle and the cannula are in a fixed positional relationship relative to each other and do not substantially slide or rotate relative to each other.

2. The port-a-cath needle of claim 1, wherein the distal junction is tapered.

3. The port-a-cath needle of claim 1, wherein the cannula has an exterior surface and the inflatable balloon is arranged to be substantially flush with the exterior surface of the cannula when the inflatable balloon is not inflated.

4. The port-a-cath needle of claim 1, wherein the inflatable balloon is positioned at the distal portion of the hollow needle.

5. The port-a-cath needle of claim 1, further comprising a squeeze bulb in fluid communication with the proximate portion of the cannula.

6. The port-a-cath needle of claim 1, further comprising a clamp wherein the clamp-restricts fluid communication with the cannula when the clamp is engaged.

7. The port-a-cath needle of claim 1, further comprising a syringe in fluid communication with the hollow needle.

8. The port-a-cath needle of claim 1, further comprising an infusion pump in fluid communication with the hollow needle.

9. The port-a-cath needle of claim 1 wherein the port-a-cath needle is configured to inflate the inflatable balloon with a medically appropriate liquid.

10. The port-a-cath needle of claim 9 wherein the medically appropriate liquid comprises saline.

11. A port-a-cath needle comprising:
    a cannula wherein the cannula has a distal portion and a proximate portion;
    a hollow needle wherein the hollow needle has a distal portion and a proximate portion; and
    an inflatable balloon, wherein the inflatable balloon is in fluid communication with the cannula and
    wherein the hollow needle is at least partially sealed within an interior of the cannula, wherein the proximate portion of the hollow needle is sealed to the proximate portion of the cannula forming a proximate junction and the distal portion of the hollow needle is sealed to the distal portion of the cannula forming a distal junction, wherein an interior of the hollow needle is isolated from the interior of the cannula, and wherein the inflatable balloon is positioned at the distal portion of the cannula,
    wherein the distal junction is tapered and wherein the cannula has an exterior surface and the inflatable balloon is arranged to be substantially flush with the exterior surface of the cannula when the inflatable balloon is not inflated
    and wherein the hollow needle and the cannula are in a fixed positional relationship relative to each other and do not substantially slide or rotate relative to each other.

12. The port-a-cath needle of claim 11, wherein the inflatable balloon is positioned at the distal portion of the hollow needle.

13. The port-a-cath needle of claim 11, further comprising a squeeze bulb in fluid communication with the proximate portion of the cannula.

14. The port-a-cath needle of claim 11 wherein the port-a-cath needle is configured to pierce a septum of a port chamber and deliver a treatment to the port chamber.

15. The port-a-cath needle of claim 11 wherein the port-a-cath needle is configured to inflate the inflatable balloon with a medically appropriate liquid.

16. The port-a-cath needle of claim 15 wherein the medically appropriate liquid comprises saline.

* * * * *